(12) United States Patent
Partti-Pellinen et al.

(10) Patent No.: US 10,017,806 B2
(45) Date of Patent: Jul. 10, 2018

(54) METHOD FOR DETERMINATION OF MICROORGANISMS

(71) Applicant: Stora Enso OYJ, Helsinki (FI)

(72) Inventors: Kirsi Partti-Pellinen, Imatra (FI); Jari Räsänen, Imatra (FI); Kielo Härmälä, Ruokolahti (FI); Anu Kettunen, Nummela (FI); Kalle-Juhani Riihinen, Espoo (FI)

(73) Assignee: Stora Enso OYJ, Helsinki (FI)

( * ) Notice: Subject to any disclaimer, the term of this patent is extended or adjusted under 35 U.S.C. 154(b) by 0 days.

(21) Appl. No.: 15/524,718

(22) PCT Filed: Oct. 27, 2015

(86) PCT No.: PCT/IB2015/058278
§ 371 (c)(1),
(2) Date: May 5, 2017

(87) PCT Pub. No.: WO2016/071805
PCT Pub. Date: May 12, 2016

(65) Prior Publication Data
US 2017/0321243 A1    Nov. 9, 2017

(30) Foreign Application Priority Data
Nov. 7, 2014 (SE) ...................... 1451333

(51) Int. Cl.
| C12Q 1/68 | (2018.01) |
| C12Q 1/04 | (2006.01) |
| C12Q 1/22 | (2006.01) |
| C12Q 1/34 | (2006.01) |
| G01N 33/34 | (2006.01) |
| C12Q 1/6806 | (2018.01) |
| D21C 5/00 | (2006.01) |
| D21H 17/00 | (2006.01) |

(52) U.S. Cl.
CPC ................. *C12Q 1/04* (2013.01); *C12Q 1/22* (2013.01); *C12Q 1/34* (2013.01); *C12Q 1/68* (2013.01); *C12Q 1/6806* (2013.01); *D21C 5/005* (2013.01); *D21H 17/005* (2013.01); *G01N 33/34* (2013.01); *C12Q 2521/531* (2013.01)

(58) Field of Classification Search
CPC ....................................... C12Q 1/04
See application file for complete search history.

(56) References Cited

U.S. PATENT DOCUMENTS

| 5,928,875 A | 7/1999 | Breen et al. |
| 2004/0014122 A1 | 1/2004 | Breen et al. |
| 2013/0189152 A1 | 7/2013 | Rice et al. |

FOREIGN PATENT DOCUMENTS

| WO | 9747764 A1 | 12/1997 |
| WO | 2004042082 A1 | 5/2004 |

OTHER PUBLICATIONS

International Search Report for PCT/IB2015/058278, dated Feb. 19, 2016.

*Primary Examiner* — Albert M Navarro
*Assistant Examiner* — Mark Navarro
(74) *Attorney, Agent, or Firm* — Greer, Burns & Crain, LTD

(57) ABSTRACT

The present invention relates to determination of the microorganism content in material comprising cellulose within the pulp and paper industry. The material comprising cellulose is enzymatically pretreated and microorganisms are determined using PCR based technology.

14 Claims, 3 Drawing Sheets

METHOD FOR DETERMINATION OF MICROORGANISMS

This application is a U.S. National Stage under 35 U.S.C. § 371 of International Application No. PCT/IB2015/058278, filed Oct. 27, 2015, which claims priority to Swedish Patent Application No. 1451333-7, filed Nov. 7, 2014.

FIELD OF INVENTION

This invention relates to a method for determination of the microorganism content in material comprising cellulose within the pulp and paper industry.

DESCRIPTION OF RELATED ART

Paper and board are important packaging materials used in many fields of industry. Packaging paper or board can provide physical or chemical protection to the object(s) enclosed; they can also e.g. provide information and enhance marketing and portion control of the objects. Paper and board have also a long history in the food industry in a multitude of uses including packaging. As a packaging material, paper often comes in direct contact with food. Paper and board containers are used for dry food, liquids and frozen products. Paper wrapping is commonly used also for fast food and candies, pharmaceuticals packaging, cigarette packaging, luxury packaging and high-class graphical products. The packaging protects the content against the action of hazardous factors of the environment thus prolonging the useful life of the packed contents. The hygiene requirement for consumer packaging board products is extremely high.

Paper and board are usually mainly composed of cellulose fibres, calcium carbonate, starch and hemicellulose. All these are natural components and can serve as growth media for contaminating microorganisms. The circulation of water having a high content on nutrients and starch is a common origin of microbial infection.

Traditionally, microbial purity of a substance has been evaluated by using microbiological methods requiring cultivation of a sample of the material or surface to be analyzed. The composition and culturing conditions (temperature, time, medium) have impact on the accuracy of the method. The sample for quantitative analysis has to be diluted to such an extent that one can count single colonies formed by cells. There may be dozens or at most a few hundreds of cells in the studied sample. The colony count in parallel samples may vary a lot and, consequently, the reproducibility is bad. Thus, the accuracy or reliability is poor. In addition, microbial methods are typically labor intensive and time consuming and thus not optimal for follow-up (monitoring) the purity of paper and board packages.

Polymerase chain reaction (PCR) based methods of identifying a microorganisms in a papermaking process including a paper sheet are know from e.g. U.S. Pat. No. 8,613,837 and US2013189152.

As the present methods are labor intensive, time consuming and their accuracy and sensitivity are not satisfying there is a need for improved methods of determining microbiological purity of paper and board material.

OBJECTS AND SUMMARY OF THE INVENTION

An object of this invention is to provide an improved method for determination of contaminating microorganisms in material comprising cellulose within the pulp and paper industry. This object is achieved by the present invention as will be described and claimed below.

The first aspect of the invention is a method for the determination of a microorganism content in material comprising cellulose within the pulp and paper industry. Characteristic features of said method are given in the characterizing part of claim 1.

The second aspect of the invention is the use of cellulase in the pretreatment of material comprising cellulose within the pulp and paper industry before determination of microorganisms using quantitative PCR.

The method allows for simple and accurate follow up of the microbiological purity of material comprising cellulose within the pulp and paper industry and also of the resulting paper and board materials, such as consumer packaging materials, especially food packaging materials. Thereby the hygiene of packaging material is enhanced since possible contaminations can be detected at an early stage.

SHORT DESCRIPTION OF THE FIGURES

DETAILED DESCRIPTION OF THE INVENTION

Figure 1:
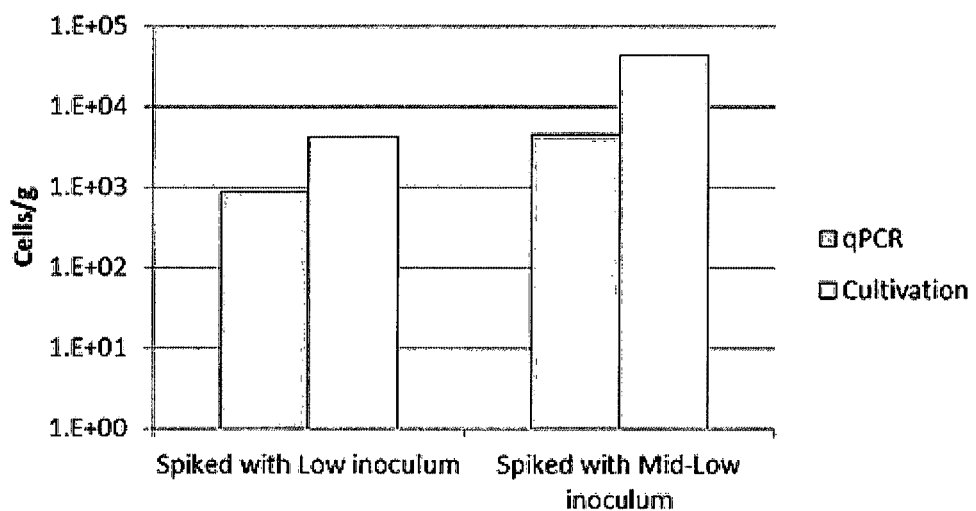
FIG. 1 shows a comparison of qPCR analysis for bacteria in inoculated board suspended in a buffer and subjected to a compression filtration and traditional cultivation for the determination of microorganisms.

The inventors have surprisingly found that the PCR based determination of microbiological purity of material comprising cellulose within the pulp and paper industry can be remarkably enhanced by enzymatic pretreatment of the sample. The enzymatic pretreatment allows quantitative detection using PCR also when the levels of contaminating microorganisms are very low.

According to the invention the determination of a microorganism content in material comprising cellulose within the pulp and paper industry comprises the steps of:
(a) providing a suspension of a sample of the material comprising cellulose; and
(b) treating the suspension of step (a) with one or more enzyme preparation(s) having cellulase activity; and
(c) separating the microorganisms from the enzyme treated suspension of step (b); and
(d) isolating nucleic acids from the separated microorganisms of step (c); and (e) conducting a PCR analysis on the isolated nucleic acids of step (d),
wherein the PCR result indicates the microorganism content of the sample.

As known within the art a positive PCR result indicates the presence of a certain nucleic acid and thus a certain microorganism whereas qPCR is used for the determination of microorganism levels.

In this connection "a microorganism content" should be understood to cover both the qualitative (e.g. identifying the microbial strain) and quantitative (e.g. the amount of colony forming units of bacteria) microorganism content of the sample. Determination of the quantitative and qualitative microorganism content in a sample material can be done independently or together. The qualitative content can be measured using primers specific to certain genera or species. Presence of the PCR product indicates presence of the microorganism and can be determined using gel electrophoresis or preferably using analytics of qPCR equipment. Quantitative determination is performed using qPCR equipment and known controls, where necessary. Either broad-range primers or specific primers can be used.

According to this invention the phrase "material comprising cellulose within the pulp and paper industry" means cellulose containing materials within the pulp and paper industry including raw materials, cellulosic material during the manufacturing process and the end products. Examples of such materials comprising cellulose (cellulosic materials) are, without limiting to those, wood chips, mechanical pulp, and various papers and boards. Pulp, various papers and boards are preferred materials. Consumer board is particularly preferred and packaging board for food and liquids is the most preferred material comprising cellulose.

In this connection the term "consumer board" includes general packaging board, food and non-food packaging board, liquid packaging board, pharmaceuticals packaging board, cigarette board and graphical board. The paper or board to be tested for microbiological purity can be singleply or multiply as well as coated or uncoated. Paper or board contains cellulosic fibres and optionally a varying amount of hemicellulose and optionally other constituents and/or coatings. The hemicellulose content or coating can have an effect on the optimal composition of the enzyme preparation. The preferred paper and board material is consumer packaging board, especially packaging board for liquids and food material.

The suspension can be taken directly from an aqueous phase of the manufacturing process. However, when the suspension is derived from a process or an aqueous product it must be ensured that the solution is suitable for the activity of enzyme preparation in the following steps. If necessary, the buffer has to be changed.

A sample of the potentially contaminated material comprising cellulose may be suspended in a solution, typically a buffer solution suitable for activity of the enzyme preparation to be used. The paper or board material can be spliced before the suspending step e.g. by using scissors. Usually the step of suspending the material of paper or board is enhanced by mechanical grinding and/or e.g. vortexing. One example of a preferred method of suspending a sample can be found in Standard Methods for the Examination of Dairy Products, 17$^{th}$ edition, APHA publications. Samples derived from pulping processes may be subjected to enzyme treatment without mechanical grinding. However, in some cases the suspension buffer has to be changed in order to meet the needs of enzymatic activity in the following step.

Thereafter, a gravimetric amount of a, preferably homogenized, suspension is contacted with an enzyme preparation containing one or more cellulase and optionally hemicellulase activities. Typically the enzyme preparation is added to the suspension.

The suspension is treated with cellulolytic enzymes in order to enhance separation of microorganisms and fibrous material. Enzyme preparation according to this invention contains at least one enzyme having cellulase activity. Optionally the enzyme preparation further contains hemicellulase activities. The enzyme preparation can also be a mixture of enzymes having cellulase activities and optionally one or more hemicellulase activities. Enzyme preparation containing several cellulase activities is preferably enriched with one or more endoglucanase activities. Cellulase enzymes can be endocellulases such as endoglucanases (EC 3.2.1.4) or exoactive cellobiohydrolases (EC 3.2.1.91), without restricting to those, and they can have also other cellulolytic and/or hemicellulolytic activities or any mixture of those. Endoglucanases are preferred. Endoglucanase activities of the cel5 family are especially useful. Hemicellulases can be e.g. xylanases (EC 3.2.1.8) or mannanases or any mixtures thereof. An example of a commercially available enzyme mixture useful in the present invention is Ecostone L900 (AB Enzymes, Finland), which is a cel5 enriched *Trichoderma* cellulase mixture.

Enzymatic treatment is gentle for living microorganisms and reduces the need for extensive mechanical grinding. It enhances separation of microorganisms and fibres in the paper or board substrates whereby the sensitivity and accuracy of the determination is enhanced.

Preferably, the Enzyme preparation is dosed in a slight excess in order to ensure proper separation of microorganisms and fibres in the material comprising cellulose. The conditions including e.g. pH, temperature and incubation time for enzymatic treatment (defined as step (b) above) should be suitable for the enzyme preparation activity. Enzymatic treatment also shows better repeatability than mechanical methods of maceration. After the enzymatic treatment, the suspension allows separation of the microorganisms from the cellulose containing material using e.g. filtration bag centrifugation.

The amount of contaminating microbiological impurities (the amount of microorganisms) in pulp derived from a properly functioning manufacturing process, or from paper or board obtained using a properly functioning manufacturing process, is typically very low. Thus it is necessary to separate the microorganisms from the remaining fibres. In principle any known method for recovering the microorganisms can be used but filtration bag centrifugation is the most preferred. A centrifuge filter bag will recover living microorganisms but remaining residual fibres will be discharged. A suitable pore size for the filter bag can be selected by a person skilled in the art and may be e.g. 50 micrometers.

Thereafter, the separated cells can be treated by propidium monoazide (PMA). PMA penetrates the membranes of dead cells and reacts with nucleic acids, resulting in DNA which cannot be amplified by PCR. Thus only the DNA from viable cells can be determined.

Then nucleic acids of the separated microorganisms are isolated. Again, any known method can be used. One example of a suitable protocol is described in Rinttilä et al.

Finally, the isolated nucleic acid material is conducted to a PCR analysis, usually to quantitative PCR (qPCR). qPCR allows both quantitative and qualitative determination of contaminating microorganism(s). A person skilled in the art is able to select suitable PCR primers for e.g. total bacterial determination; for example primers for amplifying 16S rDNA region are usable in the determination of the total bacterial content. It is also possible to use primers specific for certain genera or species of microorganisms (a qualitative analysis, optionally with also a quantitative result). Samples with amplification curve exceeding the threshold cycle before a non-template control and a valid melting curve indicate the presence of microorganisms. A quantitative PCR result is calculated using standards with a known amount/concentration of microorganisms.

When compared to traditionally used methods of cultivation qPCR is remarkably faster and not as labor intensive as cultivation. The method of the invention is also very sensitive and enables detection of small changes in microbial purity of the material. For example a liquid packaging material is deemed to be microbiologically pure when the total bacterial count per gram of liquid packaging board is less than 250 colony forming units (cfu/g) (Standard Methods for the Examination of Dairy Products, $17^{th}$ edition, APHA publications). Thus sensitivity and low detection limit are essential for usability of the method.

Improved accuracy, specificity and usability of the determination method allows continuous follow-up of the produced material on the manufacturing site and easy follow up or random testing before using the packaging material. Thus, the method according to the invention improves the safety and hygiene of consumer packaging. In addition, microbiological impurities in manufacturing processes are harmful to the process and the resulting product. Early detection of a possible increase in microbial count makes it easier to e.g. prevent formation of microbial deposits.

The method described here is suitable for determination of any type of microorganism. The method is especially suitable for determination of bacteria, especially *Bacillus* species and species within *Bacillus* D group. It is also possible to determine contaminating fungi and mold.

The use of cellulase enzyme in pretreatment of a material comprising cellulose within the pulp and paper industry before determination of microorganisms using quantitative PCR is also within scope of this invention. Cellulase enzyme can be used alone or in combination with other cellulase enzymes and/or with one or more hemicellulase enzyme(s). Both mixed cellulase preparations and so called whole cellulase preparations having several hydrolytic activities, as well as cellulases having only one or two main activities are usable within the scope of this invention. As known in the art the type of the cellulase is dependent on the type of the fibrous material. In a most preferred use paper or board material is pretreated with endoglucanase enzyme before the quantitative determination of microorganisms.

The invention is illustrated by the following non-limiting examples. It should be understood that the embodiments given in the description above and the examples are for illustrative purposes only, and that various changes and modifications are possible within the scope of the invention.

EXAMPLES

Example 1: Inoculation of Packaging Board

A bacterial strain belonging to *Bacillus* D group was grown in TSB (tryptic soy broth) overnight at +37° C. To ensure viability, bacteria were harvested during the exponential growth phase. From the primary growth broth, a volume of 5 ml was transferred to 500 ml of fresh broth and incubated at +37° C. for 6 hours. Bacterial cells were divided into 10×50 ml falcon tubes and harvested by centrifugation. All 10 bacterial pellets were re-suspended into a 5 ml sterile citric acid buffer (0.05 M, pH 5.0) and combined together and filled up to 200 ml ('Bacterial stock'). Bacterial stock was added to a board-buffer mixture at 20 µl for Low and 200 µl for Mid-Low inoculum.

A packaging board was inoculated with two levels of *Bacillus* strains belonging to *Bacillus* D group (Low and Mid-Low). Culturing was carried out according to FDA standard protocol (Standard Methods for the Examination of Dairy Products, $17^{th}$ edition, APHA publications). Serial dilution of *Bacillus* grown as explained above was used to inoculants; High-Level was 1:10 dilution, and following Mid-High, Mid-Low and Low were diluted respectively so that Low level inoculant was diluted 1:10 000.

Example 2. Propidium Monoazide Treatment

For propidium monoazide treatment, a pellet containing bacterial cells was dissolved with a hand vortex to 1980 µl of 0.9% NaCl. The resulting liquid was transferred into 2 ml Eppendorf tube and 20 µl of PMA (propidium monoazide) reaction solution was added. The tubes were manually shaken to mix the samples and then incubated for 5 min in dark @ RT without shaking. After incubation, the tubes were inverted to homogenize the samples, placed sideways on cold elements under 500 W lamp and illuminated for 5 min. Thereafter, the samples were centrifuged at 20000×g at +4° C. for 10 min (Eppendorf Centrifuge 5804 R) and the supernatant was poured away. After centrifugation, the pellet was dried in vacuum desiccator at +45° C. for 20 minutes and dissolved into 45 µl of Tris-EDTA buffer at +55° C. for 1.5-2 hours.

Example 3: DNA Extraction and qPCR

DNA extraction for cells isolated from the fibrous material was essentially carried out as described by Rinttilä et al (2004). In brief, lysis reagents were added to the tube with glass beads and FastPrep bead beater was used three times at the speed of 6.5 m/s for 1 minute. The tubes were incubated at 65° C. for 20 min, vortexing with Thermomixer every 2 minutes. 800 µl of phenol-chloroform-isoamylalcohol (24:23:1) was added, mixed and centrifuged at 10000 g for 5 min. 600 µl of liquid phase was transferred into a new tube and extracted with chloroform:isoamylalcohol (24:1). 270 µl 100% isopropanol was used to precipitate the DNA and the liquid was removed after centrifugation of 20000 g at +4° C. for 15 min. The pellet was washed twice with 1 ml (−20° C.) 70% ethanol and centrifuged with 20000 g at +4° C. for 5 minutes. After centrifugation, the pellet was dried in vacuum desiccator at +45° C. for 20 minutes and dissolved into 45 µl of Tris-EDTA buffer at +55° C. for 1.5-2 hours.

DNA samples were diluted 1:2, 1:4 and 1:8 for qPCR analysis. Broad-range primers as described in Nadkarni et al. 2002 were used for 40 cycles with an annealing temperature of 60° C. Sample results were calculated according to a standard curve based on 10-fold diluted standards.

Example 4: Compression Filtration

Packaging board inoculated with two levels of strains of *Bacillus* D group. Low and Mid-Low) as described in Example 1 was homogenized with a Waring blender into buffer and pressed with compression filtrate to separate the solid and the liquid phase. qPCR result from filtrate obtained from a compression filtration represented only 21 and 11% of the cultivation result for Low and Mid-Low inoculation level, respectively, see FIG. 1. Much lower result from the compression filtrate than cultivation result indicates that compression filtration is not an adequate separation method for microbes from packaging board.

Figure 2:
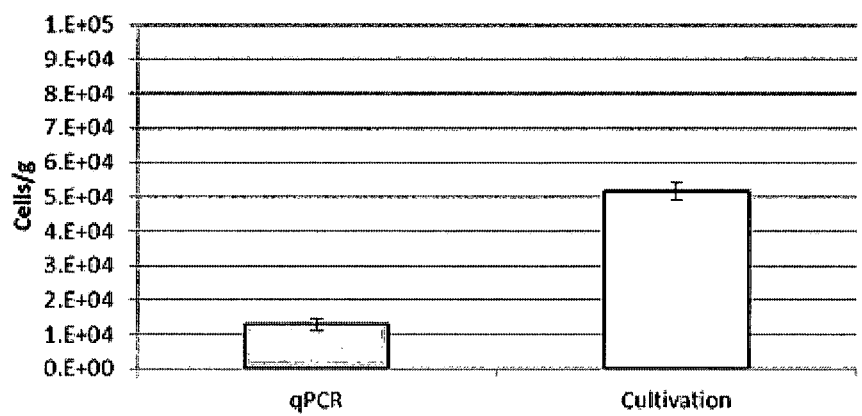
FIG. 2 shows a comparison of qPCR analysis of bacteria in inoculated board suspended in a buffer and subjected to a bag centrifugation filtration and traditional cultivation for the determination of microorganisms.

Example 5: Filtration Bag Centrifugation is an Inadequate Separation Method for Microbes Packaging board (10 g) was cut into small pieces with sterile scissors excluding the edges of the board sample. The resulting pieces were mixed with 300 ml of citric acid buffer (0.05 M, pH 5) and homogenized in a Waring blender. Known gravimetric amount of homogenized, soaking wet packaging board (35±0.1 g) was transferred into 50 ml Falcon tubing containing a filter bag (F57 filter bag for fiber and in vitro studies, Ankom Technology) and centrifugally filtered. Ideally, indissoluble matrix would be trapped in the filter bag while the bacteria would sediment into the pellet. Nevertheless, the qPCR result represented 27% of cultivation result, indicating that sole filtration bag centrifugation is not an adequate separation method for microbes from packaging board suspended into a solution. Result using qPCR and cultivation is shown as FIG. 2.

Example 6: Enzyme Treatment

Four enzyme preparations containing cellulolytic activities (so called "whole cellulases" or "mixed cellulases") were tested in relation to their capability to break down board samples suspended in a buffer. The tested enzymes were Ecostone L900 (AB Enzymes), Optimase™ CX40L, Optimase™ CX60L and Multifect (Genencor). The main activities according to manufacturers' announcements and other publicly available information are as follows: Ecostone L900 is a cel5 enriched *Trichoderma* cellulase preparation. OPTIMASE™ CX 40L enzyme preparation contains cellulase and hemicellulases as main enzyme activities. Optimase CX60L contains multiple enzyme activities but is standardized on the basis of its activity on carboxymethylcellulose (CMC). Xylanase is the main activity for Multifect.

To ensure that enzyme activities would not limit the break-down of board substrate, the following series of test settings (see Table 1) where the ratio of enzyme volume to board mass ranged from 5 to $15 \times 10^{-5}$ was carried out. The efficiency did not change even though more enzyme per board was provided indicating that already the smallest volume contained so much enzyme that the enzymatic activity did not limit the break-down of board.

TABLE 1

| Test setting | Board (g) | Buffer (ml) | Enzyme volume (μl) |
| --- | --- | --- | --- |
| 1 | 10 | 300 | 500 |
| 2 | 10 | 300 | 700 |
| 3 | 10 | 250 | 850 |
| 4 | 10 | 150 | 1500 |
| 5 | 15 | 150 | 2200 |
| 6 | 20 | 250 | 1700 |
| 7 | 15 | 250 | 1300 |
| 8 | 10 | 250 | 800 |

All enzymes were applied as maximal volume so that enzyme activity would not limit the break-down of board substrate. Incubation temperature, pH and other conditions was adjusted to optimal range for each enzyme according to recommendations of the manufacturers. The capability of the enzymes to break-down the board substrate was estimated visually and the two enzymes with cellulose as main activity were superior to the other two, indicating that celluloses are preferred over hemicellulases.

Example 7: Analysis of Spiked Packaging Boards with qPCR

Figure 3A:
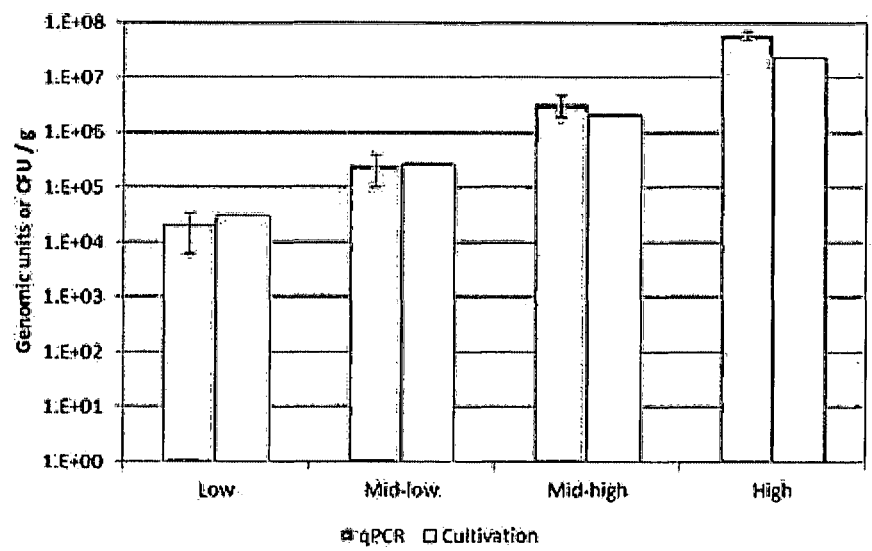
FIGS. 3a and 3b shows a comparison between the method according to the present invention and a traditional cultivation based method in the determination of microorganisms in two different papers or boards.
Figure 3B:
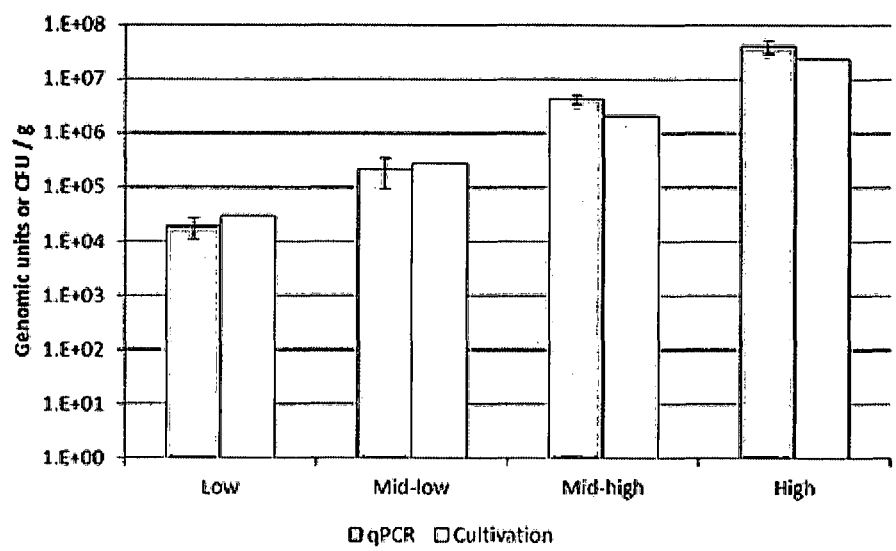

Two different packaging boards were inoculated with four levels of strains of *Bacillus* D group (Low, Mid-Low, Mid-High and High) as described in Example 1. Culturing was carried out according to FDA standard protocol (Standard Methods for the Examination of Dairy Products, $17^{th}$ edition, APHA publications). For qPCR analysis, packaging boards (10 g) were cut into small pieces with sterile scissors excluding the edges of the board sample. The resulting pieces were mixed with 300 ml of citric acid buffer (0.05 M, pH 5) and homogenized in a Waring blender. A known gravimetric amount of homogenized, soaking wet packaging board (35±0.1 g) was transferred into a storage bottle and incubated in an incubator shaker at 40° C. with a cellulase enzyme (AB Enzymes, Ecostone L900). The sample was transferred into 50 ml Falcon tubing containing a filter bag and centrifugally filtered. Indissoluble matrix was trapped in the filter bag while the bacteria sedimented into the pellet. The samples for which viable cells were to be measured were treated with propidium monoazide at the pellet stage before the lysis reagents were added. qPCR results shown in FIGS. 3a and 3b showed excellent linearity and low standard deviation between replicate samples. They were also in line with cultivation results i.e. showed good recovery and accuracy (90 and 97%, respectively). The experiment was repeated several times using various boards without inoculation. The results obtained using enzyme treatment and qPCR were in line with the respective cultivation results. Due to a very low level of endogenous microbes no statistically meaningful differences could be observed. Data is not shown.

Figure 4:
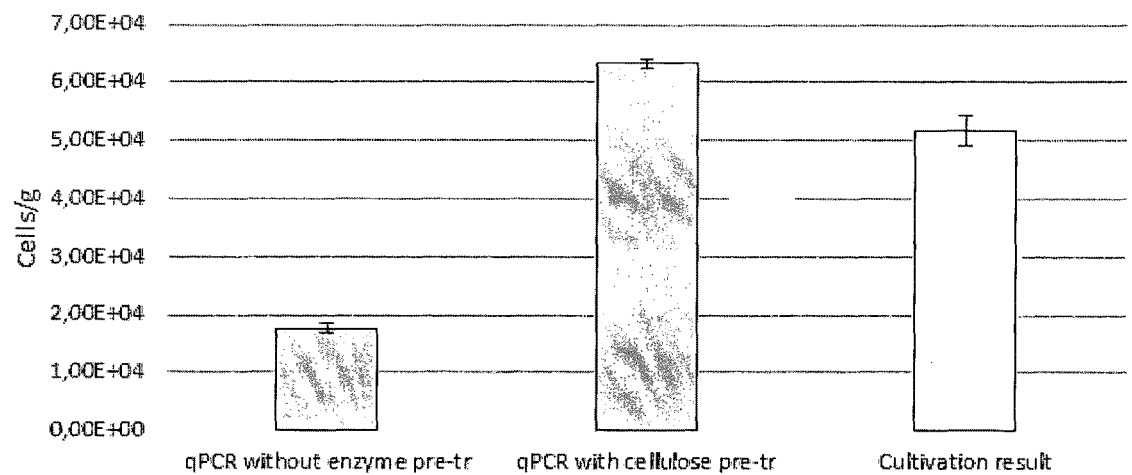
FIG. 4 shows a comparison of the method for the determination of microorganisms in board firstly using qPCR without enzymatic pretreatment, secondly according to the present invention and thirdly using a traditional cultivation based method.

Example 8: Comparison of Determination by Cultivation and qPCR with and without Cellulase Pretreatment Cultivation after suspending the board sample showed higher microbial level than the quantitative polymerase chain reaction when no enzyme pretreatment is applied prior to DNA extraction and qPCR analysis. Pretreatment with cellulose prior to the DNA extraction and qPCR analysis, however, shows good accordance to cultivation result. Filtration bag centrifugation was used to the separation of microbes before qPCR, Results are shown as FIG. 4.

Example 9: Enzyme Pretreatment as Compared to Other Pretreatments

Culturing of the packaging board samples was carried out according to the FDA standard protocol (Standard Methods for the Examination of Dairy Products, $17^{th}$ edition, APHA publications). Compression filtration was carried out as described in Example 1 and filtration bag centrifugation as described in Example 5. Enzyme treatment using commercial Ecostone L900 was carried out as described in Example 7.

Figure 5:
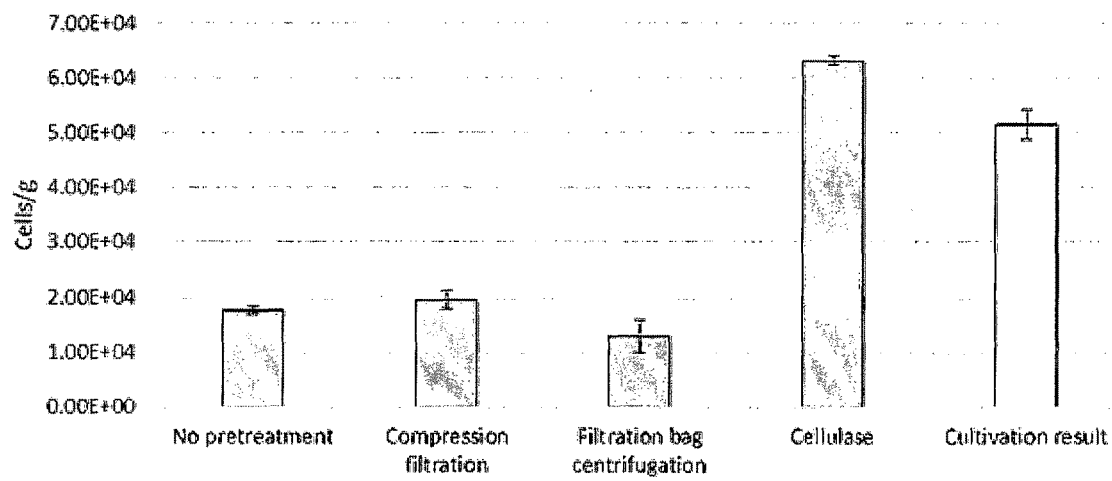
FIG. 5 shows a comparison of microorganism determination using traditional cultivation, qPCR without enzymatic pretreatment, compression filtration as pretreatment, filtration bag centrifugation as pretreatment and the method according to the present invention using two different mixed commercial cellulase preparations.

The cellulase pretreated samples showed a level respective to cultivation (similar or slightly higher) while other pretreatments (compression filtration and filtration bag centrifugation) and samples without pretreatment showed lower level as compared to cultivation. Results are shown as FIG. 5.

REFERENCES

Nadkarni, M. A., F. E. Martin, N. A. Jacques, and N. Hunter. 2002. Determination of bacterial load by real-time PCR using a broad-range (universal) probe and primers set. Microbiology 148:257-266.

Rinttilä T, Kassinen A, Malinen E, Krogius L, Palva A. Development of an extensive set of 16S rDNA-targeted primers for quantification of pathogenic and indigenous bacteria in fecal samples by real-time PCR. J. Appl. Microbiol. 2004; 97(6):1166-1177.

Standard Methods for the Examination of Dairy Products, 17$^{th}$ edition, APHA publications. 2004

The invention claimed is:

1. A method for determination of a microorganism content in a material comprising cellulose within the pulp and paper industry comprising the steps of:
   (a) providing a suspension of a sample of the material comprising cellulose; and
   (b) treating the suspension with one or more enzyme preparation having cellulase activity; and
   (c) separating the microorganisms from the enzyme treated suspension;
   (d) isolating nucleic acids from the separated microorganisms; and
   (e) conducting a PCR analysis on the isolated nucleic acids,
   wherein the PCR result indicates the microorganism content.

2. The method according to claim 1, wherein the suspension is provided by suspending a sample in a solution.

3. The method according to claim 1, wherein the cellulase activity is a mixture of cellulase activities.

4. The method according to claim 1, wherein the cellulase activity is at least one endoglucanase activity.

5. The method according to claim 1, wherein the enzyme preparation further contains hemicellulase activity or activities.

6. The method according to claim 1, wherein the microorganisms are separated from the suspension using filter bag centrifugation.

7. The method according to claim 1, wherein the primers for PCR are broad-range primers for bacteria or other microorganism.

8. The method according to claim 1, wherein the primers for PCR are specific to certain species or genus of microorganism.

9. The method according to claim 1, wherein material comprising cellulose is consumer board.

10. The method according to claim 1, wherein the microorganism belongs to bacteria.

11. The method according to claim 10, wherein said bacteria represents a *Bacillus* species.

12. The method according to claim 1 wherein the microorganism is a fungi or mold.

13. The method according to claim 1 wherein the cells are treated with propidium monoazide.

14. The method according to claim 9, wherein the consumer board material is board for the food industry.

* * * * *